United States Patent [19]

Forgione et al.

[11] Patent Number: 5,175,201
[45] Date of Patent: Dec. 29, 1992

[54] VINYL-TERMINATED CARBAMYLMETHYLATED MELAMINES, VINYL-TERMINATED POLYURETHANE/POLYAMIDE POLYMERS AND COATING/ADHESIVE COMPOSITIONS CONTAINING SAME

[75] Inventors: Peter S. Forgione, both of Stanmford, all of; Yuhshi Luh, Orange; Balwant Singh; William A. Henderson, Jr., Stamford, both of, all of Conn.

[73] Assignee: American Cyanamid Company, Stamford, Conn.

[21] Appl. No.: 264,661

[22] Filed: Oct. 31, 1988

[51] Int. Cl.$^5$ .......................... C08K 5/17; C08L 77/00
[52] U.S. Cl. ........................... 524/257; 524/271; 524/323; 524/340; 524/347; 524/358; 524/394; 524/396; 525/426; 525/454; 525/455
[58] Field of Search ........... 525/426, 454, 455; 524/530, 340, 347, 257, 271, 323, 358, 394, 396

[56] References Cited

U.S. PATENT DOCUMENTS

| | | | |
|---|---|---|---|
| 3,855,379 | 12/1974 | Araki et al. | 260/775 |
| 4,230,550 | 10/1980 | Vincent | 204/159.23 |
| 4,230,740 | 10/1980 | Moyer | 427/54.1 |
| 4,295,909 | 10/1981 | Baccei | 156/397.3 |
| 4,387,194 | 6/1983 | Ottavinai et al. | 525/454 |
| 4,708,984 | 11/1987 | Forgione et al. | 525/127 |
| 4,710,542 | 12/1987 | Forgione et al. | 525/127 |
| 4,734,462 | 3/1988 | Liedloff et al. | 525/424 |
| 4,874,859 | 10/1989 | Teissier et al. | 544/221 |

*Primary Examiner*—Ana L. Carrillo
*Attorney, Agent, or Firm*—Frank M. Van Riet

[57] ABSTRACT

Disclosed are novel nitrogen containing heterocyclic compounds and novel vinyl terminated polyurethane/-polyamide polymers together with the use of both of these compounds in a novel adhesive and coating composition. The nitrogen containing heterocyclic compounds of the invention contain two vinyl-terminated substituents and at least one carbamylmethyl substituent and have a nucleus selected from melamine, oligomers of melamine, benzoguanamine, and oligomers of benzoguanamine, glycoluril and oligomers of glycoluril. The vinyl terminated polyurethane compounds of the invention have a molecular weight of from about 3000 to about 80000, and contain at least two vinyl end groups.

20 Claims, No Drawings

VINYL-TERMINATED CARBAMYLMETHYLATED MELAMINES, VINYL-TERMINATED POLYURETHANE/POLYAMIDE POLYMERS AND COATING/ADHESIVE COMPOSITIONS CONTAINING SAME

The present invention relates to novel nitrogen containing heterocyclic compounds containing reactive functionalities inclusive of vinyl-terminated groups and carbamylmethyl groups. These compounds have general utility as monomers and crosslinking agents. This invention also includes novel vinyl-terminated polyurethane/polyamide polymers having a molecular weight of from about 3,000 to about 80,000 and containing at least two vinyl end groups. This invention also includes coating/adhesive compositions prepared from both (i) the novel nitrogen containing heterocyclic compounds of the invention, and (ii) the novel vinyl terminated polyurethane/polyamide polymers of the invention, said compositions having low temperature cure capacity.

BACKGROUND OF THE INVENTION

The prior art has described curable compositions containing melamine and benzoquanamine derivatives as crosslinking agents.

U.S. Pat. Nos. 4,708,984 and 4,710,542 describe respectively beta-hydroxyalkylcarbamylmethylated aminotriazines and alkylcarbamylmethylated aminotriazines containing curing compositions. These curing agents show generally superior detergent and salt spray resistant properties and are preferably cured at temperatures of from 150° C. to about 200° C.

U.S. Pat. Nos. 4,230,740 and 4,230,550 describe melamine compounds with pendant vinyl terminated groups and the use of such compounds in radiation cured coatings.

U.S. Pat. No. 4,295,909 describes adhesive compounds using a urethane acrylate capped prepolymer based on polybutadiene polyol or a polyamine.

U.S. Pat. No. 3,855,379 describes vinyl-terminated polyurethane polymers having a molecular weight of 2,000 to about 10,000 in bonding compositions.

Although the prior art describes melamine compounds with carbamylmethyl groups or melamine compounds with vinyl-terminated groups there is no disclosure of melamine compounds having both types of groups, or both types of groups in combination with methylol/alkoxymethyl groups on a melamine-type nucleus. Moreover, the prior art does not describe the combined use of vinyl-terminated polyurethanes/polyamides and melamine compounds with vinyl-terminated/carbamylmethyl groups in adhesive and coating compositions.

SUMMARY OF THE INVENTION

It has now been discovered that novel compounds having highly versatile and useful functionalities are nitrogen containing heterocyclic compounds having as essential pendant reactive groups: (i) at least 2 vinyl-terminated organic groups, and (ii) at least 1 carbamylmethyl group. Typically the nitrogen containing heterocyclic compounds containing the above groups are selected from melamine, oligomers of melamine, benzoguanamine, oligomers of benzoguanamine, glycoluril, oligomers of glycoluril, and mixtures thereof.

It is a further discovery of this invention that novel vinyl-terminated polyurethane/polyamide polymers having a molecular weight of from about 3,000 to about 80,000 containing at least two vinyl end groups have advantageous properties when used in combination with the nitrogen containing heterocyclic compounds of this invention.

It is a discovery of this invention that the novel heterocyclic nitrogen compounds and vinyl-terminated urethane compounds described in the preceding paragraphs are useful as essential ingredients in novel and improved low-temperature curing adhesive and coating formulations. This invention provides adhesives suitable for bonding, glass to glass, steel to steel, steel to glass, and plastic materials, including fiber reinforced sheet molding compound (SMC), to the same plastics, with little or no surface pretreatment.

DETAILED DESCRIPTION OF THE INVENTION

PART I—THE NOVEL NITROGEN CONTAINING HETEROCYCLIC COMPOUNDS

The novel compounds of the invention are nitrogen containing heterocyclic compounds containing at least 2 vinyl-terminated substituents and at least 1 carbamylmethyl substituent. Also novel are compositions of matter which contain a predominant proportion of one or more novel compounds of the invention.

The nucleus of the nitrogen containing heterocyclic compound of the invention is desirably selected from melamine, oligomers of melamine, benzoguanamine, oligomers of benzoguanamine, glycoluril, and oligomers of glycoluril. A nucleus derived from melamine, oligomers of melamine, benzoguanamine, or oligomers of benzoguanamine is preferred. A nucleus derived from melamine or oligomers of melamine is most preferred.

As used herein the word "oligomer(s)" of melamine, benzoguanamine, and glycoluril refers to amino resins prepared from these compounds by reaction with aldehydes such as formaldehyde.

The sites on the nitrogen containing heterocyclic compound nucleus not occupied by vinyl-terminated substituents or carbamylmethyl substituents may be occupied by any non-interfering substituents but it is preferred that such non-interfering substituents be methylol and/or alkylated methylol groups.

Novel Compounds based on Melamine or Melamine Oligomers

The novel melamine type compounds of the invention are represented by Formula (I) below:

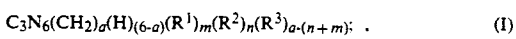

where a=3 to 6; wherein $R^1$ is a substituent selected from the group

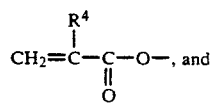

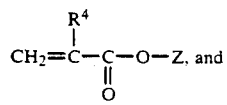

-continued $$CH_2=\overset{R^4}{\underset{|}{C}}-\underset{\|}{\overset{}{C}}NH, \text{ and}$$
$$\phantom{CH_2=C-}\overset{}{\underset{O}{\|}}$$

$$CH=\overset{R^4}{\underset{|}{C}}-CH_2-O-.$$

or mixtures thereof, and wherein Z is $CH_2CH_2-O-$ or $$-CH_2-\underset{\underset{|}{O}}{\overset{|}{CH}}-CH_3, \quad -CH_2-CH_2-\underset{\underset{|}{O}}{\overset{|}{CH_2}}.$$

$$-\underset{\underset{|}{O}}{\overset{|}{CH}}-CH_2-CH_3.$$

and wherein $R^4$ is a hydrogen or a $C_1$ to $C_{18}$ alkyl radical, and wherein $R^2$ is a carbamyl radical of the formula:

$$R^5-O\overset{O}{\underset{\|}{C}}-NH-$$

wherein $R^5$ is a $C_1$ to $C_{18}$ alkyl, alicyclic, hydroxyalkyl, alkoxyalkyl or aromatic radical, and wherein $R^3-OR^6$, wherein $R^6$ is a hydrogen or $C_1$ to $C_{18}$ aliphatic, alicyclic, or aromatic radical; with the proviso that m is at least 2, n is at least 1, and the sum of (m+n) is at least 3.

The preferred nitrogen containing heterocyclic compounds of the invention may alternatively be represented by Formula (II) below:

(II)

wherein the substituent R has the following identity:

R is acrylamido, methacrylamido, acrylate, methacrylate, $-OR^6$ where $R^6$ is as defined previously, or carbamyl; provided that at least one R substituent is carbamyl, and that at least two R substituents are selected from acrylamido, methacrylamido, allyloxy, methallyloxy, acryloyloxy, acryloyloxy alkoxy, methacryloyloxyalkoxy and methacryloyloxy.

Illustrative melamine type compounds of this invention are as follows:

$N^2,N^4,N^6$-tris(acrylamidomethyl)-$N^2,N^4,N^6$-tri-s(2-ethylhexylcarbamylmethyl)melamine $N^2,N^4,N^6$-tris(2-ethylhexylcarbamylmethyl)-$N^2,N^4,N^6$-tris(2-acryloyloxyethoxymethyl)melamine $N^2,N^4$-bis(methylcarbamylmethyl)-$N^2,N^4,N^6,N^6$-tetrakis(2-acryloyloxyethoxymethyl)melamine $N^2,N^4$-bis(methylcarbamylmethyl)-$N^2,N^4,N^6,N^6$-tetrakis(2-methacryloyloxyethoxymethyl)melamine $N^2,N^4,N^6$-tris(propylcarbamylmethyl)-$N^2,N^4,N^6$-tris(2-acryloyloxyethoxymethyl)melamine $N^2,N^4$,bis(propylcarbamylmethyl)-$N^2,N^4,N^6,N^6$-tetrakis(2-acryloyloxyethoxymethyl)melamine $N^2,N^4,N^6$-tris(propylcarbamylmethyl)-$N^2,N^4,N^6$-tris(2-methacryloyloxyethoxymethyl)melamine $N^2,N^4$,bis(methylcarbamylmethyl)-$N^2,N^4,N^6,N^6$-tetrakis(2-methacryloyloxypropyloxymethyl)melamine $N^2,N^4,N^6$-tris(acrylamidomethyl)-$N^2,N^4,N^6$-tris(methylcarbamylmethyl)melamine $N^2,N^4,N^6$-tris(methylcarbamylmethyl)-$N^2,N^4,N^6$-tris(2-acryloloxyethoxymethyl)melamine $N^2,N^4,N^6$-tris(methylcarbamylmethyl)-$N^2,N^4,N^6$-tris(2-methacryloloxyethoxymethyl)melamine $N^2,N^4,N^6$-tris(methylcarbamylmethyl)-$N^2,N^4,N^6$-tris(2-acryloloxypropyloxymethyl)melamine $N^2,N^4,N^6$-tris(propylcarbamylmethyl)-$N^2,N^4,N^6$-tris(2-methacryloloxypropyloxymethyl)melamine $N^2,N^4$-bis(propylcarbamylmethyl)-$N^2,N^4,N^6$-tetrakis(2-methacryloloxypropyloxymethyl)melamine $N^2,N^4$-bis(propylcarbamylmethyl)-$N^2,N^4,N^6$-$N^6$-tetrakis(2-acryloloxyethoxymethyl)melamine $N^2,N^4,N^6$-tris(propylcarbamylmethyl)-$N^2,N^4,N^6$-tris(acrylamidomethyl)melamine, and mixtures thereof.

Formula (I) corresponds to the melamine type compounds of the invention when m is at least 2, n is at least 1 and the sum of (m+n) is at least 3.

The novel melamine compounds of the invention include oligomeric forms of melamine represented by Formula (III) below:

wherein the degree of polymerization, p is from 2 to 10, with values of p from 2 to 5 being preferred. Oligomers of melamine are commercially available as CYMEL ® 300 series resins from American Cyanamid Company, Wayne, N.J. The melamine oligomers are typically joined by the linkage "L" shown above wherein L is a $-CH_2-$ or $-CH_2OCH_2-$ linkage which occupies sites on the melamine nucleus, however, the remaining reactive sites on the oligomeric nucleus must comply with the general requirement that at least 2 vinyl-terminated substituents and at least 1 carbamyl substituent be present.

Novel Compounds Based on Benzoguanamine and Benzoguanamine Oligomers

The novel benzoguanamine type compounds of the invention are represented by Formula (IV) below:

$$(C_6H_5)C_3N_5-(CH_2)_b(H)_{4-b}-(R^1)_m(R^2)_n(R^3)_{b-(n-m)}; \qquad (IV)$$

where b=3 to 4; wherein $R^1$, $R^2$, $R^3$, m and n are as defined in the preceding section.

Oligomeric forms of benzoguanamine having at least 2 vinyl and at least 1 carbamyl group are also compounds within the scope of this invention.

Novel Compounds based on Glycoluril and Glycoluril Oligomers

The novel glycoluril type compounds of the invention are represented by Formula (III) below:

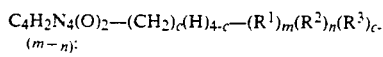

where $c = 3$ to 4; wherein $R^1$, $R^2$, $R^3$, n, and m are as defined in the preceding section.

Oligomeric forms of glycoluril having at least 2 vinyl-substituted and at least 1 carbamyl group are compounds within the scope of this invention.

Common Aspects of the Novel Nitrogen Containing Heterocyclic Compounds of the Invention The vinyl groups have been described in general terms, but may also be referred to as substituents derived from unsaturated alcohols, acids, and amides. Examples of compounds suitable for the second step of the vinyl-terminated oligomer preparation are allyl alcohol, hydroxy ethylhexyl acrylate, 2-hydroxyethyl methacrylate, 2-hydroxy propyl methacrylate, hydroxylauryl methacrylate, 2-hydroxyethyl acrylate, acrylic acid, methacrylic acid, ethacrylic acid, crotonic acid, methacrylamide, N-hydroxy acrylamide, N-hydroxy methacrylamide, acrylamide, and mixtures thereof.

The carbamylmethyl groups have been described in general terms, but may also be referred to as substituents derived from alkyl and hydroxy alkyl carbamates of from 1 to 18 carbon atoms. Examples of suitable carbamate reactants used to produce the carbamylmethyl substituents of the invention are as follows: methyl carbamate, ethyl carbamate, propyl carbamate, butyl carbamate, beta-hydroxy alkyl carbamates, 2-ethylhexyl carbamate, and beta-alkoxy alkyl carbamates.

The minimum number of vinyl-terminated substituents and carbamylmethyl substituents has been stated to be 2 and 1, respectively. However, it is generally advantageous to have a plurality of both vinyl-terminated and carbamylmethyl substituents on the compounds of the invention. In the case of melamine systems, it is desirable that each N-containing heterocyclic ring contains at least three or more vinyl groups and one or more carbamyl groups. Preferably, the heterocyclic ring should contain 3 to 5 vinyl groups and 1 to 3 carbamyl groups.

The Method of Making the Novel Nitrogen Containing Heterocyclic Compounds of the Invention The novel compounds of the invention may be prepared by the reaction of (A) alkoxymethylated or methylolated nitrogen containing heterocyclic compounds with (B) reactants consisting (i) an alkyl carbamate, and (ii) a terminally unsaturated acid, alcohol, or amide.

The nitrogen containing heterocyclic ingredient (A) may be combined with reactants (B)(i) and (B)(ii) simultaneously or in any order. Thus, reaction with alkyl carbamate may first be effected and thereafter reaction with the vinyl-terminated compound, or vice versa. In accordance with the present invention, the starting materials are reacted with alkyl carbamates, such as methyl carbamate or propyl carbamate in the presence of an acid catalyst. An illustrative reaction is depicted by the following equation (for melamine type compounds):

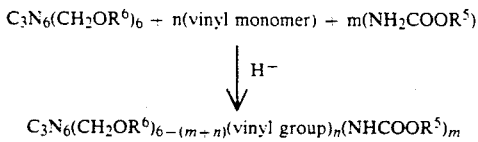

wherein vinyl is as defined above and wherein $R^5$ and $R^6$ are as previously defined and m is the desired degree of carbamylmethylation. Reaction is typically carried out by heating in the melt or in solution, e.g., in toluene, in the presence of catalytic amounts of acid such as para toluenesulfonic acid, nitric acid, sulfuric acid, and the like at temperatures between 80° C. and 150° C. Measurement of the quantity of alcohol and/or water evolved gives an indication of the degree of reaction completion. Typically, for the carbamylmethylation of melamine m is from 2 to 4, and for the carbamylmethylation of benzoguanamine or glycoluril m is 2. The method of placing carbamylmethyl substituents on the nitrogen containing heterocyclic nucleus is generally described at columns 3 and 4 of U.S. Pat. No. 4,710,542; the disclosure of which is incorporated herein by reference.

The method of placing vinyl-terminal groups on the nitrogen containing heterocyclic compounds may be found in Helv Chim Acta 24,318 E, (1941), A. Gams, G. Widmer and W. Fisch which shows a transetherification method of making allylic terminated types and U.S. Pat. No. 3,020,255 which teaches a transetherification method of making acrylic terminated derivatives. In carrying out the transetherification reaction the degree of substitution n of the vinyl-terminated groups is adjusted to be typically from 2 to 4 in the case of melamine and n equals 2 to 3 in the case of benzoguanamine or glycoluril. Suitable vinyl reactants are selected from acrylamide, methacrylic acid, methacrylamide, acrylic acid, and hydroxy functional monomers such as hydroxy alkyl acrylates and hydroxy alkyl methacrylates. The disclosure of U.S. Pat. No. 3,020,255 at columns 4 to 5 is incorporated herein by reference.

The reactions required to place vinyl-terminated groups and carbamyl groups onto the alkylmethylolated methylolated heterocyclic nucleus may be carried out simultaneously or separately and may be performed in any desired sequence.

The method of making the novel nitrogen containing heterocyclic compounds of this invention as described in this section yields a mixture of products which represent a statistical distribution of vinyl-terminated substituents and carbamylmethyl substituents. Typically, at least the predominant part by weight of the reactor product contains novel nitrogen containing heterocyclic compounds having at least two vinyl-terminated substituents and at least one carbamylmethyl substituent.

The novel compounds of the invention have general utility as resin precursors for the formation of objects and coatings, however, it is a discovery of this invention that the above described nitrogen containing heterocyclic compounds containing both vinyl-terminated substituents and carbamylmethyl substituents have special utility in preparing novel adhesive, coatings and sealant compositions. Moreover, a composition of matter which is a mixture of the novel nitrogen containing heterocyclic compounds of the invention (e.g., as prepared by the methods of this section) has special utility in preparing novel coatings, adhesives, and sealants.

PART II—THE NOVEL VINYL-TERMINATED POLYURETHANE/POLYAMIDE POLYMERS

The adhesive composition of the invention contains from about 30 to 90 weight percent of a vinyl-terminated polymer having a molecular weight of from about 3,000 to about 80,000, preferably 3,000 to 7,000, containing at least two vinyl end groups, urethane, and optionally amide linkages.

The novel vinyl-terminated polyurethane/polyamide component of the invention may be prepared by first reacting a polyisocyanate with a vinyl acid, vinyl alcohol, or vinylamide, then as a second step reacting the first step reaction product with a high molecular weight polyol.

The isocyanate material used to produce the isocyanate terminated polyurethane resin includes aliphatic, cycloaliphatic, and aromatic diisocyanates such as 2,4-tolylene diisocyanate, metaphenylene diisocyanate, 2,6-tolylene diisocyanates, p,p'-diphenylmethane diisocyanate, 1,5-naphthylene diisocyanate, phenyl diisocyanate, dianisidine diisocyanate, 1,5-naphthalene diisocyanate, 4,4'-diphenyl ether diisocyanate, p-phenylene diisocyanate, 4,4'-dicyclo-hexylmethane diisocyanate, 1,3-bis(isocyanatomethyl)cyclohexane, cyclohexylene diisocyanate, tetrachlorophenylene diisocyanate, isophorone diisocyanate, 2,6-diethyl-p-phenylenediisocyanate, 3,5-diethyl-4,4'-diisocyanatodiphenyl-methane, toluene diisocyanato-4,4'-diphenyl diisocyanate, phenylene diisocyanates, octamethylene diisocyanate, 3,3'-dimethoxy-4,4'-biphenyl diisocyanate, hexamethylene diisocyanate, tetramethyl xylylene diisocyanate (viz., TMXDI® polyisocyanate available from American Cyanamid Company, Wayne, N.J.). The preferred isocyanates are tetramethyl xylylene diisocyanate, 2,4-or 2,6-tolylene diisocyanates (2,4-TDI or 2,6-TDI), 4,4'-diphenylmethane diisocyanate (MDI)., isophorone diisocyanate (IPDI), and hexamethylene diisocyanate (HMDI).

Compounds suitable for effecting the first step reaction include vinyl alcohols, vinylic acids, and vinyl amides, hydroxy acrylates, hydroxy alkyl acrylates, and mixtures thereof. Examples of compounds suitable for the first step of the vinyl-terminated oligomer preparation are allyl alcohol, hydroxy ethylhexyl acrylate, 2-hydroxyethyl acrylate, 2-hydroxyethyl methacrylate, hydroxy propyl methacrylate, 2-hydroxypropyl acrylate, 2-hydroxybutyl acrylate, w-hydroxybutylacrylate, p-hydroxyphenyl acrylate, hydroxylauryl methacrylate, 2-hydroxypropyl methacrylate, 3-hydroxypropyl methacrylate, hydroxyhexyl acrylate, hydroxyoctyl methacrylate, the monoacrylate or monmethacrylate esters of bisphenol A, the fully hydrogenated derivatives of bisphenol A, polyethyleneglycol methacrylate, acrylic acid, methacrylic acid, ethylacrylic acid, crotonic acid, methacrylamide, acrylamide, and mixtures thereof.

The second step high molecular weight polyol reactant is typically selected from polyhydroxy functional polymeric materials which include but are not limited to polycaprolactone diols, hydroxy terminated polybutadiene polymers, hydroxy terminated poly(butadiene-acrylonitrile) polymers, hydroxy terminated poly(butadiene-styrene) polymers, multitudes of polyester polyols and polyether polyols are also suitable for this invention. The selection of the optimum polyol is dictated by specific end-user's applications. For example, the preferred polyols for plastic substrates (e.g. SMC) are the hydroxy-terminated polybutadiene and poly(butadiene-acrylonitrile) copolymers.

It is permissible to reverse the order of reaction used in the preparation of the vinyl-terminated polyurethane/polyamide polymer. Thus, in a first step reaction polyisocyanate compound is reacted with a high molecular weight polyol. Thereafter, the first step reaction product is reacted with a vinyl acid, vinyl alcohol, or vinyl amide to prepare a vinyl-terminated polyurethane/polyamide polymer substantially free of unreacted isocyanate substituents. The final vinyl-terminated polyurethane may also have additional vinyl substitution at internal positions in its structure, if desired.

The mole ratio of isocyanate groups to active hydrogen groups (e.g., $-NH_2$; $-OH$; $-COOH$) in the first step reaction is from about 1:1 to 1.1:1 with ratios of isocyanate groups to active hydrogen groups in the first plus second steps of 1:1 being preferred.

Generally, each of the two reaction steps are carried out at temperatures from 50° C. to 125° C. for a time between 0.5 to 4 hours. The preferred conditions are in the range of 60°-95° C. for 2 to 3 hours. The process may be operated in either a batch or continuous mode.

PART III—THE NOVEL COATING, SEALANT, AND ADHESIVE COMPOSITIONS

The compositions of the invention have general utility as coatings, sealants, and adhesives. All compositions of this invention contain the following essential ingredients:
(a) at least one nitrogen containing heterocyclic compound having as reactive groups; at least 2 vinyl terminated organic groups, and at least one carbamylmethyl group.
(b) at least one vinyl-terminated polyurethane/polyamide polymer having a molecular weight of from about 3,000 to about 80,000 as described in PART II of this specification.

The coating compositions and sealant compositions of this invention have as essential ingredients components A, B, C, and D as follows:
A. from about 5 to about 70 weight percent of the vinyl-terminated, carbamylmethylated nitrogen containing heterocyclic compounds of the invention.
B. from about 30 to about 90 weight percent of a vinyl-terminated polyurethane/polyamide polymer having a molecular weight of from about 3,000 to about 80.000;
C. from about 2 to about 30 weight percent of a polymerizable diluent;
D. from about 0.5 to about 5 percent of a free-radical catalyst.

wherein the sum of ingredients A, B, C and D does not exceed 100 weight percent. Preferably, the weight percent limits of the essential coating/sealant composition ingredients are as follows:
A. from 15 to 40 weight percent of the vinyl-terminated, carbamylmethylated nitrogen containing heterocyclic compound.
B. from 50 to 70 weight percent of the vinyl-terminated polyurethane/polyamide polymer.

C. from 5 to 15 weight percent of the polymerizable diluent;
D. from 0.5 to 3.0 weight percent of the free-radical catalyst.

The adhesive compositions of this invention have a essential ingredients components A, B, C, D, and E as follows:

A. from about 5 to about 70 weight percent of the vinyl-terminated, carbamylmethylated nitrogen containing heterocyclic compounds of the invention.
B. from about 30 to about 90 weight percent of a vinyl-terminated polyurethane/polyamide polymer having a molecular weight of from about 30,000 to about 80,000;
C. from about 2 to about 30 weight percent of a polymerizable diluent;
D. from about 0.5 to about 5 weight percent of a free-radical catalyst;
E. from about 0.5 to about 10 weight percent of an adhesion promoter/coupling agent.

wherein the sum of ingredients A, B, C, D and E does not exceed 100 weight percent. Preferably, the weight percent limits of the essential adhesive composition ingredients A, B, C, and D are the same as those set out for the coating/sealant composition previously described. The preferred content of ingredient E, the adhesion promoter, is from 2 to 7 weight percent.

Ingredient (A)—the nitrogen containing heterocyclic compound:

The vinyl-terminated carbamylmethylated nitrogen containing heterocyclic compounds of the invention are those described at "Part I—THE NOVEL NITROGEN CONTAINING HETEROCYCLIC COMPOUNDS:" of this disclosure. These novel compounds may be used separately or in any combination as ingredient (A) of adhesive composition described herein. In particular, ingredient (A) may be a composition of matter containing a predominant part by weight of a statistical distribution of novel nitrogen containing heterocyclic compounds of the invention, wherein said compounds have at least two vinyl-terminated substituents and at least one carbamylmethyl substituent. The novel compounds based on melamine and oligomers of melamine are particularly preferred for the formulation of compositions according to this invention.

Ingredient (B)—the novel vinyl-terminated polyurethanes/polyamides

The vinyl-terminated polyurethane/polyamides ingredient of the invention is described at "Part II—THE NOVEL VINYL-TERMINATED POLYURETHANE/POLYAMIDES POLYMERS" of this disclosure. These novel compounds are used as ingredient (B) of compositions described herein.

Ingredient (C)—the Polymerizable Diluent

The composition of the invention includes a polymerizable diluent that does not require removal during use or cure. The diluent participates in the formation of coating, sealant, or adhesive and is substantially incorporated into the cured composition.

Examples of reactive diluents useful in the practice of this invention are ethylene glycol diacrylate, ethylene glycol dimethacrylate, diethylene glycol diacrylate, diethylene glycol dimethacrylate, trimethylol propane triacrylate, trimethylol propane trimethacrylate, pentaerythritol triacrylate, pentaerythritol tetramethacrylate, 1,6-hexanediol dimethacrylate, pentaerythritol triacrylate, neopentyl glycol diacrylate, isobutoxy methacrylate (IBMA), styrene, vinyl pyrrollidone, alpha methylstyrene, meta-diisopropenylbenzene, para-diisopropenylbenzene; and mixtures thereof. Particularly preferred as reactive diluents are styrene and vinyl pyrrollidone.

The proportion of polymerizable diluent is not critical although it usually constitutes from 2 to 30 weight percent and preferably 5 to 15 weight percent of the adhesive composition. The proportion of polymerizable diluent may be adjusted to achieve a desired viscosity in the adhesive composition.

The polymerizable diluent is desirably also a solvent for the other ingredients of the adhesive composition. The term, solvent, as used herein means that the other ingredients are solubilized under the conditions of use of the composition.

Ingredient (D)—the Free-Radical Catalyst

The catalysts useful in the practice of the invention are selected from conventional free radical catalysts which decompose on heating. Generally suitable catalysts are those of the peroxide or azo type. Illustrative free-radical generating agents of the peroxide type include but are not limited to benzoyl peroxide, 2,4-dichlorobenzoyl peroxide, lauroyl peroxide, octanoyl peroxide, acetyl peroxide, dialkylperoxides such as ditert-butyl peroxide, dicumyl peroxide, ketone peroxides such as methylethylketone peroxide; and peresters which readily decompose, e.g., tertiary-butyl peracetate, tertiary butyl perbenzoate, ditertiary butyl diperphthalate, t-butyl peroxyisobutyrate, 2,5-dimethyl-2,5-di(benzoyl peroxy)hexane, 2,5-dimethyl-2,5-bis(tertiary butylperoxy)hexane-3, n-butyl-4,4-bis(tertiary butylperoxy) valerate. Another useful class of catalysts are peroxy compounds such as the organic hydroperoxides, for example, cumene hydroperoxide, cyclohexanone peroxide, methylethyl ketone hydroperoxide, tertiary butyl hydroperoxide.

The catalyst systems can optionally contain accelerators/promoters such as diethylaniline, dimethylaniline, condensation products of aldehydes and primary or secondary amines; metal salts of octyl acid, stearic acid, oleic acid, linoleic acid, naphthenic acid and rosin acid and said metal is selected from chromium, iron, cobalt, nickel, manganese and lead, lauroyl mercaptan, thiourea. Typically, from 0.1 to 5 weight percent of accelerator/promoter is used.

Particularly preferred catalysts of this invention are the azo type free radical catalysts such as alpha-alpha azo-di-isobutylronitrile.

Preferred azo polymerization initiators have the following molecular structures:

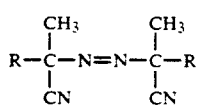

where R is methyl, ethyl, or isobutyl; and

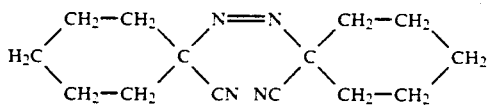

Typically, the free-radical catalysts constitute from about 0.5 to about 10.0 weight percent of the composition. The activity of the catalyst as measured by its half-life is a useful indicator of the suitability for the free radical generator for a particular application. The utility of a particular free radical catalyst may be judged by mixing it with the other components of the composition of the invention and determining the resultant shelf-life and degree of cure at the temperature of use. The catalyst may be used in microencapsulated form if desired.

Ingredient (E)—the adhesion promoter/coupling agent

The adhesive composition of the invention contains ingredients for enhancing its bonding to substrates such as steel, glass and plastics.

Useful adhesion promoting agents include silane compounds and organic anhydrides.

Silane coupling agents improve the moisture resistance, adhesion, and durability of the adhesive or coating composition prepared herein. As silane coupling agents for the present invention there may be used any conventional silane coupling agent. Preferred are silane coupling agents having a vinyl group since such materials can participate in the polymerization reactions which cure the composition of the invention. The silane compounds are typically used at concentrations of from about 0.5 to about 10.0 weight percent of the composition. Silane compounds of the following generic formula are preferred.

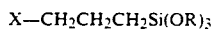

wherein X is $NH_2$, R is $C_2H_5$, or X is $CH_2=C(CH_3)CO_2$, and R is $CH_3$.

Examples of suitable silane type coupling agents are methacryloxypropyltrimethoxysilane, vinyltriethoxy silane, vinyltrimethoxy silane, vinyltris(beta-methoxyethoxy)silane, and mixtures thereof.

Stoichiometric amounts of water relative to hydrolyzable alkoxysilane groups should be present if silane compounds are incorporated into the composition without pretreatment or substrate surfaces.

The adhesion promoter may be an anhydride such as succinic anhydride, maleic anhydride, alkyl/alkenyl succinic anhydride, e.g., dodecenyl succinic anhydride, tetrahydrophthalic anhydride, hexahydrophthalic anhydride, phthalic anhydride, glutaric anhydride, 1,4,5,6,7,7-hexachlorobicyclo[2.2.1]-5-heptene-2,3-dicarboxylic anhydride, tetrachlorophthalic anhydride, 3,3',4,4'-benzophenone tetracarboxylic dianhydride, polyazelaic polyanhydride, pyromellitic dianhydride, pyromellitic dianhydride-glycol adducts, 1,2,3-cyclopentanetertcarboxylic dianhydride and mixtures thereof. Anhydrides are especially useful adhesion promoters when used with SMC.

Optional Ingredients

Additives such as stabilizers, accelerators, activators, flame retardants, pigments, plasticizers, surface active agents, dyestuff, inert filler, and other ingredients which do not adversely affect cure may be incorporated into the composition.

Packaging of Ingredients

The composition of the invention has the advantage that it may be formulated as a one-package system that has acceptable shelf-life and may be used "as is" at the time coating or adhesion is required by the user. Typically, a one-package system comprises a mixture of the essential ingredients (A, B, C, D for coating compositions or A, B, C, D, E for adhesive compositions) as described in this section.

The mixture of essential ingredients of the compositions of the invention is typically and advantageously in the form of a solution wherein the ingredients are mutually soluble under conditions of use. It is possible, however, to use the curable compositions of this invention in the form of a suspension provided that the ingredients are uniformly dispersed with one another under conditions of use.

The one package system may also contain a stabilizer to delay or prevent crosslinking of the composition ingredients during transport or storage. The stabilizers useful for this invention include hydroquinones, p-benzoquinones, anthraquinones, naphthaquinones, phenanthraquinones and substituted compounds of any of the foregoing. Additionally, various phenols can be employed such as 1,6-di-tert-butyl-4-methyl phenol, 4-methoxy phenol, 3,5-di-tert-butyl-hydroxytoluene.

The compositions of the invention may, however, be formulated as system two component packages. Typically, such a two-package system will comprise a first package containing the free-radical initiator, and the second package containing an accelerator/promoter for the selected free-radical catalyst. The two-package adhesive formulation is used by combining the packages at a time proximate to use. Method of Use:

The adhesive, sealant, and coating compositions of the invention are applied by any conventional method such as brushing, spraying, dipping, padding, or injection. The compositions are cured by application of heat, typically by convection ovens, microwave heating, or infra-red radiation. Generally, with conventional free-radical catalysts cure is effected at a temperature of from about 60° C. to 150° C. In certain instances for bonding transparent substrates (e.g., glass, certain plastics), the curing may be effected by radiation, such as ultraviolet light or ultraviolet light in combination with heat. In general surface coating applications, the curing may be effected by radiation with incorporation of radiation-sensitive catalysts. Such radiation-sensitive catalysts include camphorquinone (1,7,7-trimethyl-2,3-diketo dicyclo(2,2,1-heptane)), benzil dimethyl ketal (BDMK) benzophenone (BP), diethoxyacetophenone (DEAP), hydroxycyclohexyl phenyl ketone (HCPK), benzil diethyl ketal (2,2-diethoxy-2-phenyl acetophenone),2-isopropylthioxanthone, 2-chlorothioxanthone,1-phenyl-1,2-propanedione-2-(o-ethoxycarbonyl-)oxime, di-sec-butoxy acetophenone, benzoin isopropyl ether, methyl phenyl glyoxylate, 2-hydroxy-2,2-dimethyl acetophenone, benzoin isobutyl ether.

The preferred method of curing the compositions of the invention is by application of heat. The time of cure will depend on the specific catalyst used, but generally it is desirable to have partial cure develop within one minute.

A particular advantage of the adhesive composition of the invention is that it may be applied to the substrates to be bonded without special surface preparation. Typically, a methylene chloride wipe or light abrasion may be used as standard surface preparation. In many instances the adhesive compositions of this invention may be applied to soiled surfaces and give acceptable results.

Objects formed by the Composition of the Invention

The composition of the invention is useful in forming composites, fiber-reinforced composites laminates, adhesive interlayers, sealants, coatings, films, and solid objects. The most frequent application will be for the formation of adhesive interlayers and topcoatings.

The invention is illustrated by the following Examples.

PART ONE—PREPARATION OF THE NOVEL HETEROCYCLIC NITROGEN COMPOUNDS OF THE INVENTION, INGREDIENT (A)

EXAMPLE 1

This Example illustrates the preparation of the novel compounds of the invention.

A 2 liter flask was flushed with dry air and charged with the following ingredients:
- 158.4 grams of hexamethoxymethylmelamine (CYMEL® 300, product of American Cyanamid Company, Wayne, N.J.)
- 210.9 grams of 2-ethylhexyl carbamate
- 86.4 grams of acrylamide
- 1.35 grams of hydroquinone
- 600 milliliters of cyclohexane The reaction flask was equipped with a condenser and trap. Initially the flask contents were heated in a 90° C. bath until they became clear, then 4.5 grams of para-toluenesulfonic acid was added to the flask.

The reaction was monitored by watching the methanol byproduct accumulate in the trap. When methanol collection stopped, methanol was removed from the trap and weighed.

The reaction was concluded when the amount of methanol collected reached the approximate theoretical methanol yield. For this reaction the theoretical methanol yield was achieved about three and one-half hours after the addition of the para-toluenesulfonic acid.

The cyclohexane was removed by rotary evaporator and the flask contents reconstituted with 500 milliliters of $CH_2Cl_2$. Thereafter, the para-toluenesulfonic was neutralized with 100 milliliters of 5% by weight sodium bicarbonate solution. The organic layer was separated and dried over anhydrous potassium monocarbonate. Finally, the product was filtered and the solvent removed under vacuum (30° C. at 10 millimeters Hg pressure) to give a final product of melamine acrylamide carbamate (hereinafter called compound "M".)

The product yield was 350 grams mainly consisting of melamine substituted with 3 carbamylmethyl substituents and 3 acrylamide substituents (tris-2-ethylhexyl-carbamylmethyl, tris-acrylamidomethyl melamine).

EXAMPLE 2

A 250 ml flask was flushed with dry air and charged 19.5 g of Cymel®, 21.6 g of 2-ethylhexyl carbamate, 0.012 g of phenothiazine and heated to 95° C. for 15 minutes to get a clear solution. Thereafter, 0.28 g of p-toluenesulfonic acid was added and heating was continued for 15 minutes. The pressure was gradually lowered to 50 mm. Hg to collect MeOH distillate. When the theoretical amount of distillate was collected, the reaction mixture was cooled to 65° C. and 15.0 g of 2-hydroxyethyl acrylate was added to the reactor with stirring. The pressure was reduced to 50 mm. Hg to collect MeOH byproduct. At the end of 45 minutes, no more MeOH came out and the reaction was stopped. To the cooled reaction products was added 100 ml of $CH_2Cl_2$. Two separate 25 ml washes of 5% wt. $Na_2CO_3$ solution was used to neutralize p-toluenesulfonic acid. The organic layers were separated and dried over anhydrous $K_2CO_3$. The above mixture was filtered and the solvent was removed to give 42 g of a final product of melamine acrylate carbamate (hereinafter called compound "M1").

EXAMPLE 3

To a 250 ml 3-neck round-bottomed flask was charged 39 g of Cymel® 300, 0.018 g of phenothiazine and 30 g of 2-hydroxyethylacrylate. A distillation head and mechanical stirrer were connected to the flask. The system was flushed with dry air.

The contents of the reaction flask were heated at 65° C. and 0.35 g of p-toluenesulfonic acid (p-TSA) immediately added thereto. The reaction was run at 65° C. under vacuum pressure of 30 mm. Hg to remove methanol byproduct. At the end of 45 minutes, 8.6 g of methanol was collected and the reaction stopped. To the cooled reaction product was added 50 ml of $CH_2Cl_2$, and the product was then washed with two 25 ml portions of 5% wt $Na_2CO_3$ solution. The $CH_2Cl_2$ solution of product was dried over anhydrous $K_2CO_3$. Filtration of solids and removal of solvent gave 48 g products of melamine acrylates (hereinafter called compound "M2"). The product mainly consisted of melamine substituted with 3 ethylacrylate substituents and no carbamate groups.

EXAMPLE 4

This Example illustrates the preparation of the novel compounds of the invention.

A 3 liter flask was flushed with dry air and charged with the following ingredients:
- 823.5 grams of hexamethoxymethylmelamine (CYMEL® 300, product of American Cyanamid Company, Wayne, N.J.)
- 316.5 grams of methyl carbamate
- 0.36 grams of phenothiazine The reaction flask was equipped with a condenser and trap. Initially the flask contents were heated in a 75° C. bath for 15 minutes to get a clear solution, then 10.6 grams of para-toluenesulfonic acid was added to the flask.

The pressure of the reaction was gradually lowered from 200 to 50 millimeters of Hg to assist collection of metahnol distillate. After the theoretical amount of methanol distillate was collected (after about 60 minutes) the immersion oil bath around the flask was cooled to 65° C. Thereafter, 979 grams of 2-hydroxyethyl acrylate was added with stirring to the reaction mixture. The pressure was again reduced gradually from 200 to 25 mm. of Hg and the methanol byproduct collected.

The reaction flask was cooled and 1200 milliliters of $CH_2Cl_2$ added to the contents. 20 grams of sodium bicarbonate dissolved in 300 milliliters of water was added to the flask contents to neutralize the remaining para-toluenesulfonic acid. The resultant organic reaction layer was separated and dried over anhydrous potassium carbonate.

The dried product was filtered and solvent removed by vacuum distillation at a pressure of 1 millimeter Hg at 30° C. to 40° C. to give a final product of melamine acrylate carbamate (hereinafter called compound "M3".)

The product yield was 1851 grams consisting of mainly melamine substituted with two carbamylmethyl substituents and four ethylacrylate substituents (bis-carbamylmethyl, tetrakis(2-acryloyloxyethoxy)methyl melamine).

EXAMPLE 5

A one liter flask was flushed with dry air and charged 205.8 g of Cymel ® 300, 295 g of 2-hydroxypropylmethacrylate (HPMA, Rocryl 410 from Rohm and Haas Company) and 0.1 g of phenothiazine and heated to 75° C. for 15 minutes to get a clear solution. 2.6 g of p-toluenesulfonic acid was added and heating continued for 15 minutes. The pressure was lowered to 50 mm. Hg for MeOH byproduct collection. When the theoretical amount of distillates was collected, the reaction was cooled to 65° C. 79 g of methyl carbamate was charged and the reaction mixture stirred at 75° C. at 50 mm. Hg vacuum to collect MeOH. After 90 minutes, no more MeOH was generated and the reaction was stopped. To the cooled reaction products were added 300 ml of $CH_2Cl_2$ A two part 50 ml wash of 5% wt $Na_2CO_3$ solution was used to neutralize the p-TSA. The organic layers were separated and dried over anhydrous $K_2CO_3$. Filtration and removal of solvent gave 370 g of final product of melamine methacrylate carbamate (hereinafter called compound "M4").

Other examples of resins containing carbamylmethyl and vinyl groups based on alkylated formaldehyde derivatives of melamine, benzogunamine and glycoluril are given in Examples 6 to 17. These Example preparations are based on the generalized procedure described below.

General Procedure

A round bottom reaction flask was equipped with a mechanical stirrer and a trap with condenser suitable for vacuum distillation was charged with the reactants. The reaction mixture was heated in an 80° C. oil bath until the reactants were molten, then acid catalyst was added (usually 1-2 wt % $H_2SO_4$).

The reaction was monitored by the collection of alcohol via continuous vacuum distillation. The reaction was concluded when alcohol distillation had ceased. In cases where the amount of alcohol collected was below the theoretical, it was advisable to use a second addition of catalyst.

Because the reactivity of carboxylic acids is low compared with carbamates and alcohols, it was desirable that a 20% to 40% excess of carboxylic acid be used. Any unreacted material was removable by increasing the vacuum before concluding the reaction.

After the contents of the reaction flask were cooled to near room temperature, 350 ml of $CH_2Cl_2$ was added in preparation for the work-up of the product. The methylene chloride solution was gently washed in a separatory funnel with 5% sodium bicarbonate solution to neutralize and extract the acid. The organic phase was separated and dried over anhydrous sodium sulfate until the solution had cleared. Finally, the solution was vacuum filtered through the Buchner funnel and the solvent removed on a rotary evaporator.

| Example | Reactants | Product substituents on Cymel/mole | Conditions temperature: time, catalyst |
|---|---|---|---|
| TABLE OF TEST RESULTS FOR EXAMPLES 6 TO 10 CYMEL ® HEXAMETHOXYMETHYL MELAMINE SERIES ||||
| 6 | Cymel ® -300, 150 g (0.385 mole) methyl carbamate, 57.8 g (0.769 mole) acrylic acid, 110.9 g (1.54 mole) | 174 g 2 carbamylmethyl 2 carylate | 75° C., 5 hrs. 0.8% $H_2SO_4$ |
| 7 | Cymel ® -300, 150 g (0.385 mole) methyl carbamate, 57.8 g (0.769 mole) alpha-methyl acrylic acid, 132.5 g (1.54 mole) | 145 g 2 carbamylmethyl 2 methacrylate | 75° C. 5.5 hrs. 1.0% $H_2SO_4$ |
| 8 | Cymel ® -300, 150 g (0.385 mole) n-propylcarbamate, 119.0 g (1.16 mole) acrylic acid, 83.2 g (1.16 mole) | 184 g 2.7 carbamyl propyl 1.9 acrylate | 80° C., 4.0 hrs. 0.8% $H_2SO_4$ |
| 9 | Cymel ® -300, 150 g (0.385 mole) n-propylcarbamate, 119.0 g (1.16 mole) alpha-methyl acrylic acid, 99.3 g (1.16 mole) | 175 g 1.7 carbamyl propyl 2.0 methacrylate | 75° C., 8.0 hrs. 0.8% $H_2SO_4$ |
| 10 | Cymel ® -300, 150 g (0.385 mole) methyl carbamate, 578 g (0.769 mole) acrylic acid, 166.4 g (2.31 mole) | 190 g 2.0 carbamyl methyl 3.1 acrylate | 70° C., 7.0 hrs. 0.8% $H_2SO_4$ (grad. incr. to 1.35% $H_2SO_4$) |
| TABLE OF TEST RESULTS FOR EXAMPLES 11 TO 14 CYMEL ® BENZOGUANAMINE SERIES ||||
| 11 | Cymel ® -1123, 150 g (0.384 mole) methyl carbamate, 68.9 g (0.917 mole) acrylic acid, 66.2 g (0.917 mole) | 144 g 2.0 carbamyl methyl 1.7 acrylate | 75° C., 5.5 hrs. 0.5% $H_2SO_4$ |
| 12 | Cymel ® -1123, 150 g (0.384 mole) n-propyl carbamate, 47.3 g (0.459 mole) alpha-methyl acrylic acid, 120 g, (1.30 mol3) | 172 g 1.0 carbamyl propyl 2.8 methacrylate | 80° C., 7.5 hrs. 0.8% $H_2SO_4$ (grad. incr. to 2.0% $H_2SO_4$) |
| 13 | Cymel ® -1123, 100 g (0.256 mole) 2-hydroxyethyl acrylate 106.5 g (0.917 mole) methyl carbmate 23.0 g (0.306 mole) | 118 g 2.7 oxyethylacrylate 1.0 carbamyl methyl | 80° C., 4.5 hrs. 1.0% $H_2SO_4$ |
| 14 | Cymel ® -1123m 100 g (0.256 mole) methyl carbamate, 19.2 g (0.256 mole) acrylic acid, 100 g (1.30 mole) | 102 g 1.0 carbamyl methyl 2.8 acrylate | 80° C., 9 hrs. 1% $H_2SO_4$; incr. to |

-continued

| Example | Reactants | Product substituents on Cymel/mole | Conditions temperature: time, catalyst |
|---------|-----------|-----------------------------------|----------------------------------------|
|         |           |                                   | 1.7% H$_2$SO$_4$ |

TABLE OF TEST RESULTS FOR EXAMPLES 15 TO 17
CYMEL ® 300 BUTYLATED GLYCOLURIL SERIES

| Example | Reactants | Product substituents on Cymel/mole | Conditions temperature: time, catalyst |
|---------|-----------|-----------------------------------|----------------------------------------|
| 15 | Cymel ®-1170, 150 g. (0.309 mole) methyl carbamate, 23.2 g (0.309 mole) alpha-methacrylic acid, 93.0 g (1.08 mole) | 144 g 1.0 carbamyl methyl 2.0 methacrylate | 70° 20 C., 5 hrs. 0.5% p-TSA |
| 16 | Cymel ®-1170, 100 g. (0.206 mole) methyl carbamate, 15.5 g (0.206 mole) hydroxyethylacrylate, 71.6 g. (0.617 mole) | 111 g 1.0 carbamyl methyl 2.0 oxyethylacrylate | 70° C., 4 hrs. 1.0% p-TSA 0.25% H$_2$SO$_4$ |
| 17 | Cymel ®-1170, 100 g (0.206 mole) propyl carbamate, 21.2 g (0.206 mole) acrylic acid, 52.0 g (0.721 mole) 1.5 | 122 g 1.0 propyl acrylate | 75° C. 5.5 hrs. 1.5% p-TSA |

(1) Cymel ® 300, 1123 and 1170 are trademarks of American Cyanamid Company, Wayne, New Jersey.
(2) Substitution determined by proton NMR @ 60 mHz.

PART TWO—PREPARATION OF THE NOVEL VINYL-TERMINATED OLIGOMER OF THE INVENTION (Ingredient B)

EXAMPLE 18

This Example illustrates the preparation of a vinyl terminated oligomer used in the preparation of compositions of the invention.

A one liter glass reactor was flushed with dry air and charged with the following ingredients:
0.02 grams of phenothiazine
140.6 grams of meta-tetramethylxylylene diisocyanate The contents of the reaction flask were heated at 80° C. for 10 minutes and 0.15 grams of T-12 (dibutyltin dilaurate) catalyst added. Thereafter, 73.4 grams of 2-hydroxyethyl acrylate were gradually added over a period of thirty minutes and the reaction mixture stirred for one hour at 80° C.

143 grams of polycaprolactone diol polymer (CAPA 200 diol, molecular weight 550; product of Interox Chemicals Ltd.) were added to the reaction mixture in 4 portions over a period of thirty minutes. Stirring of the reaction mixture was continued for another one and one-half hours at 80° C.

320 grams of reaction product of urethane acrylates was collected and labeled, "H Oligomer".

EXAMPLE 19

This Example illustrates the preparation of a vinyl-terminated oligomer used in the preparation of compositions of the invention.

A 500 ml glass reactor was flushed with dry air and charged with the following ingredients:
0.02 grams of benzoquinone
14.6 grams of meta-tetramethyl xylylene diisocyanate The contents of the reaction flask were heated at 80° C. for 10 minutes and 0.10 grams of T-12 (Dibutyltin dilaurate) catalyst added. Thereafter, 7.66 grams of 2-hydroxyethyl acrylate were gradually added over a period of thirty minutes and the reaction mixture stirred for one hour at 80° C.

90 grams of poly(butadiene-acrylonitrile) copolymer (Hycar HTBN 1300x 29, product of Goodrich Tire Company) were added to the reaction mixture in 6 portions over a period of thirty minutes. Stirring of the reaction mixture was continued for another one and one-half hours at 80° C.

100 grams of reaction product of urethane acrylates was collected and labeled, "HT-M Oligomer".

EXAMPLE 20

A one liter flask was flushed with dry air and charged with 0.06 g of benzoquinone and 43.8 g of tetramethylxylylene diisocyanate. The mixture was stirred for 10 minutes at 80° C. An 0.3 g of T-12 (dibutyltin dilaurate) was added to the reaction mixture, and immediately added 26.6 g of hydroxypropyl methacrylate over a period of 30 minutes. The reaction mixture was stirred at 80° C. for one hour, then 270 g of Hycar HTBN 1300×29 (polybutadiene-acrylonitrile) copolymer was added in six portions within 30 minutes. Stirring was continued at 80° C. for another 1 and ½ hours. The reaction was thereafter stopped and the reaction products were poured into suitable containers while hot. 330 grams of reaction product of urethane methacrylates were collected and labelled, "HT-MM Oligomer".

PART THREE—TESTS OF THE ADHESIVE PROPERTIES OF THE COMPOSITIONS OF THE INVENTION

SINGLE COMPONENT SYSTEMS

EXAMPLE 21

Basestock adhesives were prepared from a mixture of 70 parts of HT-M, product of Example 19, 25 parts of M3, product of Example 4, 5 parts of N-vinylpyrrolidone (NVP), 5 parts of succinic anhydride, and 30 parts of IMSIL ® 15 Silica, product of Illnois Minerals Co. Several one package formulations comprising the above materials, various initiators, and stabilizers, were used to bound Rockwell 9468 Polyester Plastic Panels SMC. The assemblies were press heated at 250° F. (121.1° C.) for two minutes and the cooled assemblies were post-baked at 110° C./30 minutes. Wedge tests for the basestock adhesives were conducted as follows:

SMC TO SMC BONDING

The following test procedure was used to evaluate SMC to SMC adhesive bonding for Example 21 and all following Examples.

Commercial polyester plastic SMC panels (from suppliers such as Rockwell International, Diversitech, etc.) were cut into 1" by 4" (2.54 cm by 10.16 cm) coupons for bonding test uses. The bond area of the coupons were wiped with a dry rag without any pretreatment. Enough adhesive was applied to cover a 1" by 1" (2.54 cm by 2.54 cm) overlap area. 30 mil (0.762 mm.) glass beads were scattered on surface of the adhesive (in an amount not to exceed covering more than 1% of surface area). 30 mil spacers (0.762 mm.) (metal shim or Teflon ® strip) was used in one end of the test assembly to assure a uniform 30 mil (0.762 mm.) adhesive bond line. The wedge assemblies with spacers inserted and wrapped with a protective mylar film web is made ready for placement in a heated press. The assemblies were press heated 1-2 minutes at 250° F. (121.1° C.). Desirable pressure is usually 8-10 psi (6.56 to 0.70 kg/cm$^2$). After the initial 1-2 minute heating the assemblies were tested for green strength by letting the assembled coupons cool to about room temperature and thereafter hand wiggling the coupons to see that they do not readily separate (pass the test). Thereafter the spacer was removed and excessive adhesive trimmed from exposed edges. Finally, the bonded assemblies were postbaked at 300° F. (148.9° C.) for 30 minutes, then removed and cooled. A 45° angle wedge test of the assemblies was performed to determine the type of adhesive failure modes. Types of failure modes were reported as follows: Fiber Tear (FT), Adhesive Failure (AF), Cohesive Failure (CF), Stock Break (SB).

For the lap shear test, a lap configuration of assemblies was used. The adhesive bonds were 1"×1" (2.54 cm by 2.54 cm.) with 30 mil (0.76 mm.) spacers. The assemblies were press heated at 250° F. (121.1° C.) for 1-2 minutes to observe green strength. All bonded assemblies were postbaked at 300° F. (148.9° C.) for 30 minutes. The assemblies were removed and cooled. A lap shear measurement by Instron machine was performed at a crosshead speed of 0.05 in/min. (1.27 cm/min) by ASTM Method D-1002).

The test results obtained from the single component system of Example 21 are shown in the following table:

TABLE OF EXAMPLE 21 RESULTS

| Formulation | Compositions | | | Wedge Result |
|---|---|---|---|---|
| | Base Adhesive X | Initiator | Stabilizer | |
| 21A | 100 part | 1 part Vazo-52 | 220 ppm p-benzoquinone (BQ) | 95% FT |
| 21B | 100 part | 1 part Vazo-64 | 10 ppm BQ | 90% FT |
| 21C | 100 part | 1 part Benzoyl peroxide | 50 ppm BQ | 100% FT |
| 21D | 100 part | 1 part Vazo-52 | 450 ppm BQ | 95% FT |
| 21E | 100 part | 1 part Vazo-64 | 200 ppm BQ | 100% FT |

*Vazo-52 ®, Vazo 64 ®, catalyst. Product of E. I. DuPont de Nemours and Co., Inc.

EXAMPLE 22

The above formulations 21 A to E were held in room temperature storage. The aged adhesives were then checked by the same procedures as above in Example 42. Wedge results of Rockwell 9468 SMC-to-SMC bonding test obtained for formulations 21 A to E are listed below. The results show that the adhesive formulations are stable at room temperature up to 90 days.

| Formulation | Wedge Results | | |
|---|---|---|---|
| | 30 day storage | 45 day storage | 90 day storage |
| 21A | 100% FT | 85% FT | |
| 21B | 80% FT | S.B. | 95% FT |
| 21C | 90% FT | 95% FT | |
| 21D | | 95% FT | 95% FT |
| 21E | | 85% FT | 90% FT |

EXAMPLE 23

The following adhesive formulations with different compositions were used to bond SMC coupons (rag wipe only). The assemblies were press heated at 250° F. (121.1° C.) for one minute. The cooled assemblies were postbaked at 300° F. (148.9° C.) for 30 minutes. The wedge test results are tabulated below:

TABLE OF EXAMPLE 21 RESULTS

| Formulation | Compositions | | | | | Fillers | Others | Substrate | Wedge Result |
|---|---|---|---|---|---|---|---|---|---|
| | A | B | C | D | E | | | | |
| 23A | M3 24.60 g | HT-M 64.36 g | NVP 12.72 g | V-64 2.11 g | S.A. 4.56 g | Imsil/A-15 104.83 g | p-BQ 200 ppm | Rockwell 9468 Diversitech 0113 | 100% F.T. 95% F.T. |
| 23B | M3 24.60 g | HT-M 64.36 g | NVP 12.72 g | V-64 2.11 g | S.A. 4.56 g | Imsil/A-15 104.83 g | p-BQ 200 ppm | Rockwell 9468 | 100% F.T. |
| 23C | M3 12.41 g | HT-M 30.23 g | STY 6.03 g | V-64 0.98 g | M.A. 2.15 g | Imsil/A-15 47.22 g | Cab-o-sil ® TS720 0.98 g | Rockwell 9468 | 95% F.T. |
| 23D | M3 36.40 g | HT-M 96.60 g | NVP 18.80 g | V-64 2.75 g | S.A. 6.80 g | Talc 156 111.71 g | Cab-o-sil ® TS720 2.75 g | Rockwell 9468 | 95% F.T. |
| 23E | M3 19.91 g | HT-M 27.33 g | NVP 5.40 g | V-64 0.89 g | S.A. 1.94 g | Imsil/A-15 44.53 g | | Rockwell 9468 | 80% F.T. |

A, B, C, D, E as defined in text. Part III - the essential ingredients of the invention for adhesive compositions
S.A. = succinic anhydride
M.A. = maleic anhydride
p-BQ = p-benzoquinone
NVP = N-vinyl pyrrolidone
STY = styrene
CAB-O-SIL ®, fumed silica, product of Cabot Corp.
IMSIL ®, A silica, product of Illinois Minerals Co.

EXAMPLE 24

Formulations 23A and 24B previously described were used to bond Rockwell 9468 SMC coupons. The adhesives were cured in the same fashion as Example 23. Lap shear measurements of the cured assemblies were performed at 180° F. (82.2° C.) The data are listed below.

| Formulation | Lap shear data |
|---|---|
| 23A | >330 psi*, (23.20 Kg/cm$^2$) S.B. |
|  | 340 psi, (23.90 Kg/cm$^2$) 95% F.T. |
| 23B | >360 psi*, (25.31 Kg/cm$^2$) S.B. |
|  | 320 psi, (22.50 Kg/cm$^2$) 100% F.T. |

*The lap shear strength measurement could not be continued because stock broke.

EXAMPLE 25

The above formulations 23A and 23B were used to bound Rockwell 9468 SMC coupons. The adhesives were cured in the same fashion as in Example 23. The cured assemblies were soaked in the deionized water at 54° C. for 7 days. At the end of the seventh day, the assemblies were air dried and subject to wedge test and lap shear measurement at room temperature. The results are tabulated below.

| Formulation | Wedge result | Lap shear data |
|---|---|---|
| 23A | 100% F.T. | 340 psi, (25.31 Kg/cm$^2$) 100% F.T. |
| 11B | 95% F.T. | 450 psi, (31.64 Kg/cm$^2$) S.B. (100% F.T.) |

TWO COMPONENT SYSTEMS

EXAMPLES 26 TO 38

Two base stock adhesives, 26A and 26B, were formulated according to the following compositions.

| Formulation | Compositions | | | | | |
|---|---|---|---|---|---|---|
| 26A | HT-M 96.60 g | M3 36.40 g | NVP 18.80 g | S.A. 6.80 g | Imsil ® A15 155.43 g | Cab-o-sil ® TS720 3.17 g |
| 26B | HT-MM 96.70 g | M3 36.10 g | NVP 18.80 g | S.A. 6.80 g | Imsil A15 155.23 g | Cab-o-sil ® TS720 3.17 g |

HT-M is a vinyl-terminated polyurethane/polyamide oligomer prepared by the method of Example 19.
M3 is a melamine derivative prepared by the method of Example 4.

The two-component adhesive system comprises:
Part A with initiators (e.g., hydroperoxides, or peroxides); and
Part B with promoters/accelerators (e.g., transition metal complexes, or tertiary aromatic amines).

Several two-component adhesives were formulated by using base adhesives 26A and 26B with different initiator/promoter combinations. An equal weight of Part A and Part B formulations were mixed thoroughly. The well-mixed adhesives were applied to Rockwell 9468 SMC coupons. The cure conditions were the same as Example 23. The resultant pot life of the mixed adhesives and the results of wedge test on the assemblies are tabulated below.

TABLE OF RESULTS FOR TWO COMPONENT SYSTEMS

| Formulation | Part A | Part B | Pot Life | Wedge Results |
|---|---|---|---|---|
| 27 | 26A 10 g CHPO 0.20 g | 26A 10 g CoNaph 0.40 g | >60 min. | 100% F.T. |
| 28 | 26B 10 g CHPO 0.20 g | 26B 10 g CoNaph 0.40 g | >60 min. | 100% F.T. |
| 29 | 26A 10 g CHPO 0.20 g P-BQ 400 ppm | 26A 10 g CoNaph 0.40 g p-BQ 100 ppm | >60 min. | 95% F.T. |
| 30 | 26B 10 g CHPO 0.20 g p-BQ 600 ppm | 26B 10 g CoNaph 0.40 g p-BQ 200 ppm | >60 min. | 99% F.T. |
| 31 | 26A 10 g, CHPO 0.30 g | 26A 10 g, CoNaph 0.30 g | 90 min. | 100% F.T. |
| 32 | 26A 10 g, CHPO 0.40 g | 26A 10 g, CoNaph 0.30 g | 55 min. | 100% F.T. |
| 33 | 26A 10 g, CHPO 0.40 g | 26A 10 g, CoNaph 0.40 g | 45 min. | 100% F.T. |
| 34 | 26A 10 g, CHPO 0.40 g | 26A 10 g, CoPent 0.40 g | 20 min. | 100% F.T. |
| 35 | 26A 10 g, CHPO 0.40 g | 26A 10 g, CoPent 0.20 g | 35 min. | 100% F.T. |
| 36 | 26B 10 g, CPO 0.40 g | 26B 10 g, DMA 0.30 g | >60 min. | 100% F.T. |
| 37 | 26B 10 g,t-BPO 0.40 g | 26B 10 g, DMA 0.40 g | >60 min. | 100% F.T. |
| 38 | 26B 10 g, Lupersol DDM-9 0.08 g | 26B 10 g, CoNaph 0.14 g | >60 min. | 100% F.T. |

CHPO = cumyl hydroperoxide
CoNaph = 50% wt Cobalt(II) naphthenate solution in NVP
CoPent = Cobalt(II) pentanedionate
CPO = di-cumyl peroxide
DMA = Dimethyl aniline
t-BPO = di-t-butyl peroxide
BPO = benzoyl peroxide

GLASS TO STEEL BONDING

The following procedure was employed to evaluate the adhesives of the invention for glass to steel bonding applications:

Substrates

1"×4"×¼" (2.54 cm×10.16 cm×1.27 cm) plate glass coupons and
1"×4" (2.54 cm×10.16 cm) #25 cold rolled GM steel coupons.

Pretreatment

Glass coupons were dipped into silane I solution (as described below) for 5 minutes. The air dry coupons were baked at 110° C. for 12 minutes. Steel coupons were treated with tin hydrosol (as described below) for 5 minutes and dried in open air. Then the steel coupons were dipped into silane I solution for 5 minutes and dried in air, followed by baking at 110° C. for 12 minutes. The adhesives of various formulations were applied in ½" by 1" (1.27 cm by 2.54 cm) overlap with 2 mils (0.051 mm.) of thickness. The adhesives were cured at 110° C. for 30 minutes.

(1) Silane I solution—was prepared by adding to a 500 ml beaker 139.7 g. of absolute ethanol and 74.9 g. of water, and the pH adjusted with aqueous acetic acid to 5. 5.3 g. of 3-methacryloxypropyl trimethoxysilane was added dropwise into the solution with stirring for 15 minutes. The final solution was used for pretreatment of substrates as described above.

(2) Tin hydrosol—was prepared by dissolving 1 g. of $SnCl_4H_2O$ in deionized water to make one weight percent solution. Stannous chloride was then added to the resultant solution in two steps: (i) 2.5 g. $SnCl_2$ was added, then (ii) 1.0 g. $SnCl_2$ was added. Each $SnCl_2$ addition was carried out at room temperature with stirring to ensure complete dissolution before the next addition. The final tin hydrosol solution was used for pretreatment of substrates as described above. The lap shear data are tabulated in the following Table:

TABLE 4
TEST RESULTS OF EXAMPLES 39 TO 44

| Example | Adhesive Formulation | Compositions A | B | C | D | Lap shear strength |
|---|---|---|---|---|---|---|
| 39 | I | M 0.40 g | H 1.30 g | NVP 0.30 g | V-52 0.02 g | 2100 psi (147.6 Kg/cm$^2$) |
| 40 | J | M1 0.4 g | H 1.30 g | NVP 0.30 g | V-52 0.02 g | 1900 psi (119.5 Kg/cm$^2$) |
| 41 | K | M2 0.4 g | H 1.30 g | NVP 0.30 g | V-52 0.02 g | 1400 psi (98.4 Kg/cm$^2$) |
| 42 | I1 | M 0.1 g | H 1.30 g | NVP 0.60 g | V-52 0.02 g | 2100 psi (147.6 Kg/cm$^2$) |
| 43 | J1 | M1 0.1 g | H 1.30 g | NVP 0.60 g | V-52 0.02 g | 1400 psi (98.4 Kg/cm$^2$) |
| 44 | K1 | M2 0.1 g | H 1.30 g | NVP 0.60 g | V-52 0.02 g | 1000 psi (70.3 Kg/cm$^2$) |

The results show the superior performance of carbamylated acryl adhesives containing M (formulations I and I1) and M1 (formulations J and J1) over the non-carbamylated ones containing M2 (formulations K and K1).

GLASS TO GLASS BONDING

Substrates
1"×4"×¼" (2.54 cm by 10.16 cm by 0.635 cm) plate glass coupons

Pretreatment:

Glass coupons were dipped into Silane I solution for 5 minutes. The air dried coupons were baked at 110° C. for 12 minutes. To the cooled coupons were applied adhesive in a 1" by ½" (2.54 cm by 1.27 cm) overlap 2 mils (0.051 mm.) thick. The adhesives were cured at 110° C. for 30 minutes.

The lap shear data are listed below.

| Example | Adhesive Formulation | Lap shear strength |
|---|---|---|
| 45 | I | 1900 psi (133.6 Kg/cm$^2$) |
| 46 | J | 1500 psi (105.5 Kg/cm$^2$) |
| 47 | K | 400 psi (28.1 Kg/cm$^2$) |

The results showed that adhesives containing crosslinkers M and M1 of this invention gave better bond strength than M2, the non-carbamylated acrylmelamine.

STEEL TO STEEL BONDING

Substrate
1" by 4" (2.54 cm by 10.16 cm) #25 cold rolled GM steel coupons.

Pretreatment:

Steel coupons were degreased by $CH_2Cl_2$ wipe, followed by dipping the coupons into silane II solution (as described above) for 5 minutes. The air dry coupons were baked at 110° C. for 12 minutes. These pretreated coupons were used for application of adhesives. Adhesive I was applied on the above pretreated steel coupons with a 1"×½" (2.54 cm by 1.27 cm) overlap. Adhesive thickness was 5 mil (0.127 mm.). The adhesive-bound coupons were cured at 110° C. for 30 minutes. Adhesives J and K were applied and cured in a similar fashion.

Silane II solution—was prepared as Silane I solution, supra, except that 139.7 g. of absolute ethanol, 7.4 g. of water, and 3 g. of alpha-aminopropyltriethoxy silane were used. The final solution was used for pretreatment of substrates as described below.

The lap shear data of the cured coupons by Instron testing were tabulated below:

| Example | Adhesive Formulation | Lap shear strength |
|---|---|---|
| 48 | I | 1600 psi (1) (112.5 Kg/cm$^2$) |
| 49 | J | 1350 psi (94.9 Kg/cm$^2$) |
| 50 | K | 1100 psi (77.3 Kg/cm$^2$) |

(1) psi = pounds per square inch.

The results show the bond strength of adhesives containing vinyl-terminated carbamylalkylated melamines M and M1, is stronger than non-carbamylalkylated M2.

Overbake Effect on Adhesive Bonds

Substrate:
1"×4" (2.54 cm by 10.16 cm) #25 cold rolled steel coupons

Pretreatment

Following the same procedure as in Examples 48–50 for steel pretreatment, the adhesives are applied in ½"×1" (1.27 cm by 2.54 cm) overlap 2 mils (0.0508 mm.) thick, and cured at 110° C. for 30 minutes. Some cured specimen were further overbaked at 200° C. for another 30 minutes. The lap shear data of both 110° C./30 minutes cure and 200° C./30 minutes overbake samples are summarized below.

| Cure conditions of Adhesive Formulations | | | |
|---|---|---|---|
| Example | Formulation | 100° C./30 min cure | 200° C./30 min overbake |
| 51 | I | 2250 psi (158.2 Kg/cm²) | 2150 psi (151.2 Kg/cm²) |
| 52 | K | 2150 psi (151.2 Kg/cm²) | 1800 psi (126.6 kg/cm²) |

The results show that the adhesives containing carbamylated acrylate melamine compound of this invention (M in formulation I) retained 95% of original bond strength after overbake at 200° C./30 min. However, the adhesives containing non-carbamylated acrylated melamine (M2 in formulation K) lost 16% of its original bond strength after overbake. These results show better thermal stability of adhesives prepared from the novel ingredients and combination of essential ingredients used in this invention over those prepared from analogous non-carbamylated compounds.

It is to be expected that numerous modifications will readily become apparent to those skilled in the art upon reading this description. All such modifications are intended to be included within the scope of the invention as defined in the appended claims.

We claim:

1. A curable coating/sealant composition comprising:
   A. from about 5 to about 70 weight percent of at least one nitrogen containing heterocyclic compound having as reactive groups at least two vinyl-terminated organic groups, and at least one carbamylmethyl group;
   B. from about 30 to about 90 weight percent of a vinyl-terminated polymer, containing urethane, and optionally amide linkages, and having a molecular weight from about 3000 to about 80,000;
   C. from about 2 to about 30 weight percent of a polymerizable diluent;
   D. from about 0.5 to about 5 weight percent of a free-radical catalyst;
   wherein the sum of A, B, C and D does not exceed 100 weight percent.

2. The composition of claim 1 wherein the nucleus of the vinyl terminated carbamylated nitrogen containing heterocyclic compound (A) is selected from the group consisting of melamine, oligomers of melamine, benzoguanamine, oligomers of benzoguanamine, glycoluril, oligomers of glycoluril, and mixtures thereof.

3. The composition of claim 1 wherein the vinyl-terminated carbamylmethylated nitrogen containing heterocyclic compound of part (A) is an melamine-type compound having a nucleus represented by the formula:

where a=3 to 6; wherein R¹ is a substituent selected from the group consisting of:

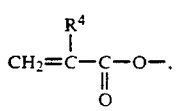

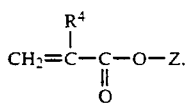

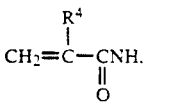

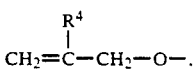

and mixtures thereof, and wherein Z is CH₂CH₂—O— or

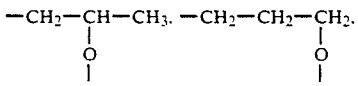

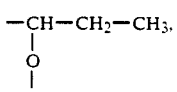

and wherein R⁴ is a hydrogen or a C₁ to C₁₈ alkyl radical, and wherein R² is a carbamyl radical of the formula:

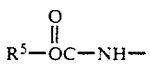

wherein R⁵ is a C₁ to C₁₈ alkyl, alicyclic, hydroxyalkyl, alkoxyalkyl or aromatic radical, and wherein R³ is —OR⁶, wherein R⁶ is a hydrogen or C₁ to C₁₈ aliphatic, alicyclic, or aromatic radial; with the proviso that m is at least 2, n is at least 1, and the sum of (m+n) is at least 3.

4. The composition of claim 1 wherein the vinyl-terminated carbamylmethylated nitrogen containing heterocyclic compound of part (A) is a glycoluril type compound represented by the formula:

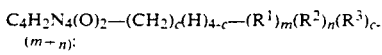

wherein c is 3 to 4; and wherein R¹ is a substituent selected from the group

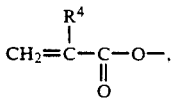

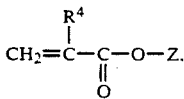

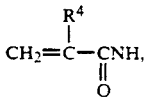

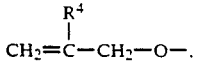

or mixtures thereof, and wherein Z is CH₂CH₂—O—,

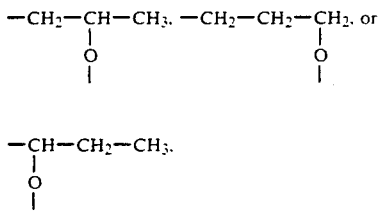

and wherein $R^4$ is a hydrogen or a $C_1$ to $C_{18}$ alkyl radical, and wherein $R^2$ is a carbamyl radical of the formula:

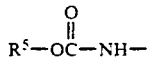

wherein $R^5$ is a $C_1$ to $C_{18}$ alkyl, alicyclic, hydroxyalkyl, alkoxyalkyl or aromatic radical, and wherein $R^3$ is $-OR^6$, wherein $R^6$ is a hydrogen of $C_1$ to $C_{18}$ aliphatic, alicyclic, or aromatic radical; with the proviso that m is at least 2, n is at least 1, and the sum of (m+n) is at least 3.

5. The composition of claim 1 wherein the vinyl-terminated carbamylmethylated nitrogen containing heterocyclic compound of part (A) is a benzoguanamine type compound represented by the formula:

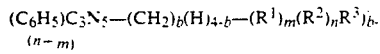

wherein b = 3 or 4; and wherein $R^1$ is a substituent selected from the group

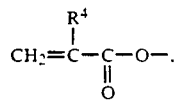

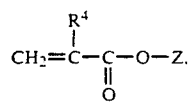

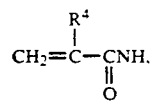

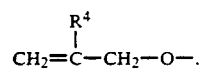

or mixtures thereof, and wherein Z is $CH_2CH_2-O-$,

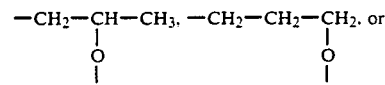

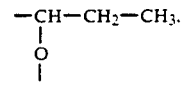

and wherein $R^4$ is a hydrogen or a $C_1$ to $C_{18}$ alkyl radical, and wherein $R^2$ is a carbamyl radical of the formula:

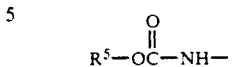

wherein $R^5$ is a $C_1$ to $C_{18}$ alkyl, alicyclic, hydroxyalkyl, alkoxyalkyl or aromatic radical, and wherein $R^3$ is $-OR^6$, wherein $R^6$ is a hydrogen or $C_1$ to $C_{18}$ aliphatic, alicyclic, or aromatic radical; with the proviso that m is at least 2, n is at least 1, and the sum of (m+n) is at least 3.

6. The composition of claim 1 wherein the vinyl-terminated carbamylmethylated nitrogen containing heterocyclic compound of part (A) is selected from the group consisting of the following:

$N^2,N^4,N^6$-tris(acrylamidomethyl)-$N^2,N^4,N^6$-tris(2-ethylhexylcarbamylmethyl)melamine $N^2,N^4,N^6$-tris(2-ethylhexylcarbamylmethyl)-$N^2,N^4,N^6$-tris(2-acryloyloxyethoxymethyl)melamine $N^2,N^4$-bis(methylcarbamylmethyl)-$N^2,N^4,N^6,N^6$-tetrakis(2-acryloyloxyethoxymethyl)melamine $N^2,N^4$-bis(methylcarbamylmethyl)-$N^2,N^4,N^6,N^6$-tetrakis(2-methacryloyloxyethoxymethyl)melamine $N^2,N^4,N^6$-tris(propylcarbamylmethyl)-$N^2,N^4,N^6$-tris(2-acryloyloxyethoxymethyl)melamine $N^2,N^4$,bis(propylcarbamylmethyl)-$N^2,N^4,N^6,N^6$-tetrakis(2-acryloyloxyethoxymethyl)melamine $N^2,N^4,N^6$-tris(propylcarbamylmethyl)-$N^2,N^4,N^6$-tris(2-methacryloyloxyethoxymethyl)melamine $N^2,N^4$,bis(methylcarbamylmethyl)-$N^2,N^4,N^6,N^6$-tetrakis(2-methacryloyloxypropyloxymethyl)melamine $N^2,N^4,N^6$-tris(acrylamidomethyl)-$N^2,N^4,N^6$-tris(methylcarbamylmethyl)melamine $N^2,N^4,N^6$-tris(methylcarbamylmethyl)-$N^2,N^4,N^6$-tris(2-acryloloxyethoxymethyl)melamine $N^2,N^4,N^6$-tris(methylcarbamylmethyl)-$N^2,N^4,N^6$-tris(2-methacryloloxyethoxymethyl)melamine $N^2,N^4,N^6$-tris(methylcarbamylmethyl)-$N^2,N^4,N^6$-tris(2-acryloloxypropyloxymethyl)melamine.

$N^2,N^4,N^6$-tris(propylcarbamylmethyl)-$N^2,N^4,N^6$-tris(2-methacryloloxypropyloxymethyl)melamine $N^2,N^4$-bis(propylcarbamylmethyl)-$N^2,N^4,N^6$-tetrakis(2-methacryloloxypropyloxymethyl)melamine $N^2,N^4$-bis(propylcarbamylmethyl)-$N^2,N^4,N^6$-$N^6$-tetrakis(2-acryloloxyethoxymethyl)melamine $N^2,N^4,N^6$-tris(propylcarbamylmethyl)-$N^2,N^4,N^6$-tris(acrylamidomethyl)melamine, and mixtures thereof.

7. The composition of claim 1 wherein the vinyl-terminated (B) has a molecular weight of from about 3000 to about 80000, and contains at least two vinyl end groups, said polymer produced by the process of reacting in a first reaction step polyisocyanate with a high molecular weight polyol; then in a second step, reacting the first step reaction product with a vinyl acid, vinyl alcohol, or vinyl amide.

8. The composition of claim 7 wherein the vinyl-terminated polymer (B) polyisocyanate reactant is selected from the group consisting of 2,4-tolylene diisocyanate, metaphenylene diisocyanate, 2,6-tolylene diisocyanate, p,p'-diphenylmethane diisocyanate, 1,5-naphthylene diisocyanate, phenyl diisocyanate, dianisidine diisocyanate, 1,5-naphthalene diisocyanate, 4,4'-diphenyl ether diisocyanate, p-phenylene diisocyanate, 4,4'-dicyclohexylmethane diisocyanate, 1,3-bis(isocyanatomethyl)- cyclohexane, cyclohexene diisocyanate, tetrachlorophenylene diisocyanate, isophorone diisocyanate, 2,6-diethy-p-phenylenediisocyanate. 3,5-diethyl-4,4'-diisocyanatodiphenyl-methane, toluene diisocyanato-4,4'-diphenyl diisocyanate, phenylene diisocyanates, octamethylene diisocyanate, 3,3'-dimethoxy-4,4'-biphenyl diisocyanate, hexamethylene diisocyanate, tetramethyl xylylene diisocyanate and mixtures thereof.

9. The composition of claim 1 wherein the vinyl terminated polymer (B) having a molecular weight of from about 3000 to about 80000 contains at least two vinyl end groups; said polymer produced by the process of reacting polyisocyanate with a vinyl acid, vinyl alcohol, or vinyl amide; then, in a second step reacting the first step reaction product with a high molecular weight polyol.

10. The composition of claim 9 wherein the vinyl acid, vinyl alcohol and vinyl amide are selected from the group consisting of allyl alcohol, hydroxy ethylhexyl acrylate, 2-hydroxyethyl acrylate, 2-hydroxyethyl methacrylate, hydroxy propyl methacrylate, 2-hydroxypropyl acrylate, 2-hydroxybutyl acrylate, 2-hydroxybutylacrylate, p-hydroxyphenyl acrylate, hydroxylauryl methacrylate, 2-hydroxypropyl methacrylate, 3-hydroxypropyl methacrylate, hydroxyhexyl acrylate, hydroxyoctyl methacrylate, the monoacrylate or monmethacrylate esters of bisphenol A, the fully hydrogenated derivatives of bisphenol A, polyethyleneglycol methacrylate, acrylic acid, methacrylic acid, ethylacrylic acid, crotonic acid, methacrylamide, acrylamide, and mixtures thereof.

11. The composition of claim 1 wherein the polymerizable diluent (C) is selected from the group consisting of: ethylene glycol diacrylate, ethylene glycol dimethacrylate, diethylene glycol diacrylate, diethylene glycol dimethacrylate, trimethylol propane triacrylate, trimethylol propane trimethacrylate, pentaerythritol triacrylate, pentaerythritol tetramethyacrylate, 1,6-hexanediol dimethacrylate, pentaerythritol triacrylate, neopentyl glycol diacrylate, isobutoxy methacrylate (IBMA), styrene, vinyl pyrrollidone, alpha methylstyrene, meta-diisopropenylbenzene, para-diisopropenylbenzene; and mixtures thereof.

12. The composition of claim 1 wherein the free-radical catalyst is selected from the group consisting of peroxide catalyst, and azo catalysts.

13. The composition of claim 1 which contains a cure promoting effective amount of an accelerator/promotor.

14. The composition of claim 13 wherein the accelerator/promotor is selected from the group consisting of diethylaniline, dimethylaniline, condensation products of aldehydes and primary or secondary amines, lauroyl mercaptan, thiourea and; metal salts of octyl acid, stearic acid, oleic acid, linoleic acid, naphthenic acid and rosin acid and where said metal is selected from chromium, iron, cobalt, nickel, manganese and lead.

15. The composition of claim 1 in the form of a one package system.

16. The composition of claim 13 in the form of a two package system wherein the free-radical catalyst (D) is in one package and the accelerator/promotor is in the other package.

17. The composition of claim 1 containing from 0.05 to 2 weight percent of a stabilizer.

18. The composition of claim 12 wherein the stabilizer is selected from the group consisting of hydroquinones, p-benzoquinones, anthraquinones, naphthquinones, phenanthraquinones, 1,6-di-tert-butyl-4-methyl phenol, 4-methoxy phenol, and 3,5-di-tert-butylhydroxytoluene.

19. The composition of claim 1 wherein ingredient (A), the heterocyclic compound is from 15 to 40 weight percent of the composition, and ingredient (B) the vinyl-terminated polymer is from 50 to 70 weight percent of the composition.

20. The composition of claim 1 wherein the ingredient (C) polymerizable diluent is from 5 to 15 weight percent of the composition.

* * * * *